Nov. 17, 1953 F. W. HOF MANN Plant Pat. 1,230
NECTARINE TREE
Filed April 5, 1952
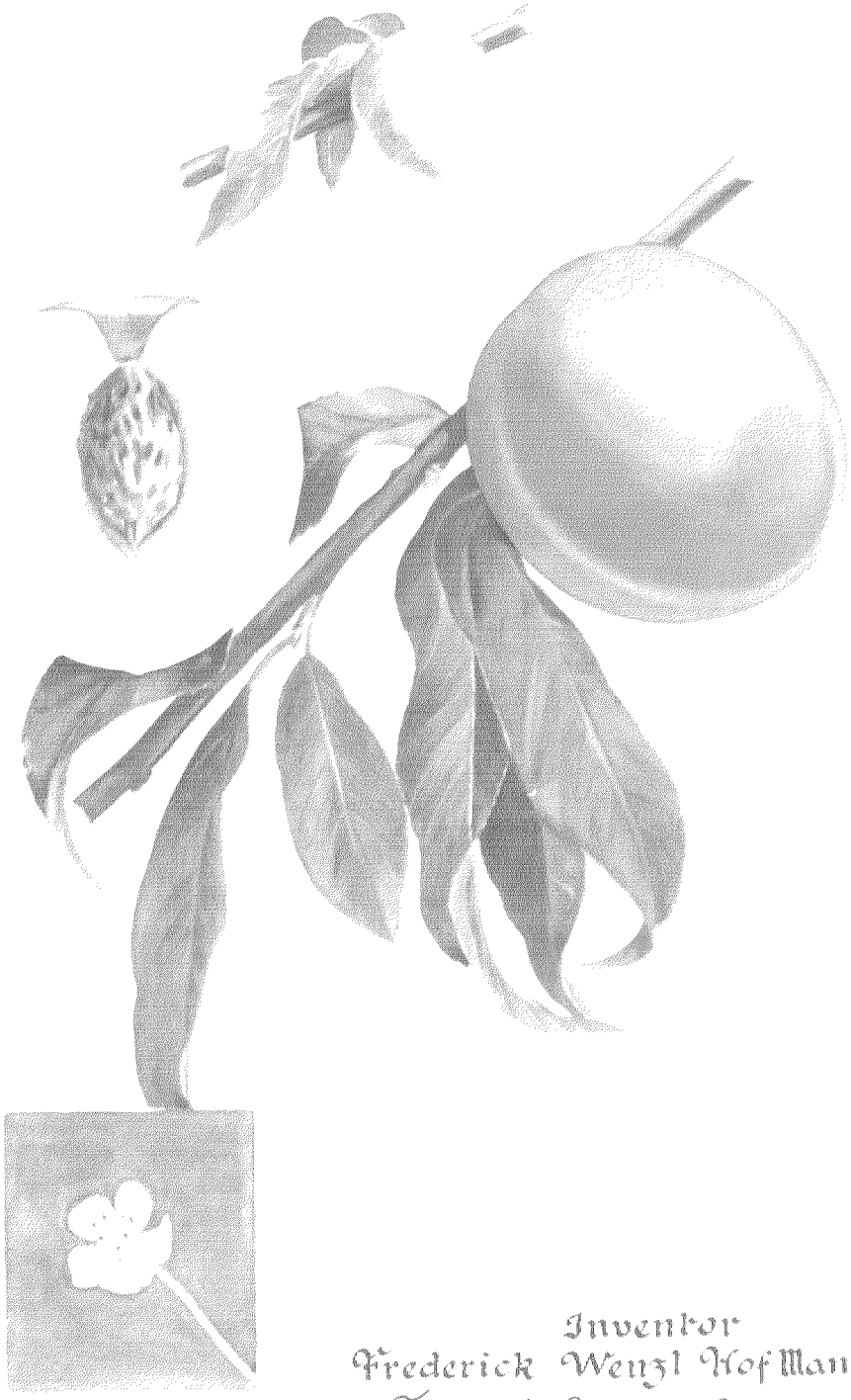
Inventor
Frederick Wenzl Hofmann
by Talbert Dick & Adler
Attorneys Patented Nov. 17, 1953 Plant Pat. 1,230

UNITED STATES PATENT OFFICE 1,230

NECTARINE TREE

Frederick Wenzl Hof Mann, Omaha, Nebr.

Application April 5, 1952, Serial No. 280,779

1 Claim. (Cl. 47—62)

My invention relates to a new and distinct variety of nectarine tree.

This tree has been developed by a selection from several thousand inbreds from the nectarine tree described and claimed in my Plant Patent 479, and the development work leading to this new variety was carried on in the State of Nebraska. The inbred selected was a result of self-pollination of Plant Patent 479 and my new variety has been successfully asexually reproduced by budding to establish the characteristics which I will now describe.

In general form and appearance, this new tree is very similar to the Elberta, unpatented, with the exception that its fruit has a plum-like, waxy, and smooth or non-fuzz surface or skin, the same as Plant Patent 479. However, its new and outstanding characteristic resides in its unusual tolerance to lead arsenical sprays.

Experience with nectarines has demonstrated that they are highly susceptible to damage from the insect known as curculio that lays its eggs in the fruit. All well known standard nectarine varieties are very susceptible to lead arsenical injuries without certain safening materials. Lead arsenical sprays have proved one of the most effective materials for the control of curculio worm infestation. A nectarine strain that is able to tolerate lead arsenical sprays to the greater degree is to that extent more promising for a larger crop prospect of highly finished marketable fruit. With sufficient spray coverage of adequate amounts of lead arsenate, the chances are far more likely for an almost 100 per cent curculio worm control and a relatively larger crop of well finished fruit. Experiments to establish this characteristic of tolerance to arsenical sprays consisted of three (3) separate set-ups at three different locations in Omaha, Nebraska, observed through 1948–1949, 1949–1950, 1950–1951, 1951–1952 and for purposes of identification herein, the new tree made the subject of this application will be referred to as Sib 3. Each of the three (3) set-ups mentioned was composed of twelve (12) Elberta grafts made on Sib 3 along with Sib 3 limbs and twelve (12) grafts of Sib 3 on Elberta along with Elberta limbs. Each pair to be compared for observation was paired in such a manner that only the effect of the spray dosage used was to be compared. In addition to the above grafts, six (6) trees of Elberta and six (6) of Sib 3 were compared and observations were made of trees of J. H. Hale, not patented, Sunglo, not patented, Polly, not patented and Hardie, Plant Patent 120.

In each of the years 1949–1951 inclusive, all limbs of the Elbertas and all limbs of the J. H. Hale, Sunglo, Polly and Hardie were significantly injured by the arsenical sprays while no significant injury was observed to the grafts or limbs of Sib 3. Thus, from these experiments it can be concluded that this new nectarine strain can tolerate lead arsenical spray causticity to a greater degree than any of the well known standard nectarine varieties and because of this characteristic can produce relatively larger crops of properly finished fruit. Because of its characteristics entirely different from that of any of the well known standard varieties, the possibilities of growing nectarines under a greater variety of conditions than heretofore are relatively enhanced.

In addition to the above, this new variety compares favorably with the tree in Plant Patent 479 as an improvement over the Elberta in winter hardiness, in greater resistance of the fruit buds to winter kill and in greater hardiness to any freeze injuries.

In this respect observations were made of the three set-ups above described. One set-up was located on very low ground and subject to the more extreme of winter rigor. In the season 1947–1948 observations over the greater part of the Omaha vicinity were also made. There was no Elberta peach crop in the general vicinity for that season. In the lower location there was in this season no crop of Elberta, Hale, Sunglo or Polly but a very satisfactory crop of the progeny or sibs of Plant Patent 479 of which Sib 3 is one. Evidence of the observations for this season was such that it can be concluded that these sibs had a greater fruit bud hardiness against fruit bud winter killing that is so prevalent through this general Omaha vicinity. In the season of 1948–1949 there was another commercial crop failure in this vicinity for all of the above varieties except the sibs mentioned above. Elberta, Hale, Sunglo and Polly merely had a scant crop that would be regarded a commercial failure. In the season 1949–1950 all crops were slightly better but the best results were with the above mentioned sibs. Season 1950–1951 much like the previous season. Season 1951–1952 still showed better crop results for all the above mentioned sibs of which Sib 3 is one. Sib 3 came out so consistently without a bloom and fruit crop failure that it can be concluded it is hardier for the conditions that cause the killing of peach fruit buds over the winter period.

This fruit may also be harvested, packed and shipped with little, if any, brown rot break-down, as compared to the Elberta and when picked after maturity into a fully tree ripened fruit, will store and ship very well. Its shape holds up well for canning purposes for which it is suitably adapted because of its tasty flavor and firm texture. This resistance to brown rot was also apparent from the three set-ups mentioned above. Each set-up as previously indicated had grafted limbs of Sib 3 on Elberta trees and grafted limbs of Elberta on Sib 3 trees. The twelve Elberta limbs and Sib 3 limbs were directly compared on a parallel and corresponding basis. Likewise in the three locations comparisons of the trees of these two varieties were compared in as close a proximity as planting distance would permit. Conditions for exposure to brown rotting of fruit was the same for one variety as for the other. Observations were made of the fruit crops on the trees up to harvest and then at different periods after harvesting including ordinary room temperature and cooler temperature storage and also under conditions of parcel post transits.

Observations were made through the seasons 1948–1949, 1949–1950, 1950–1951 and 1951–1952. In some seasons there were only very scant Elberta crops that would be ordinarily regarded as commercial failure crops but there were enough of the Elberta fruits during these periods even during the scant years to allow for studies to determine the brown rot holding up properties.

The 1949–1950, the 1950–1951 and the 1951–1952 seasons were the most striking. The 1949–1950 Elberta crop was almost a total loss due to brown rot even on the trees before harvest while there was no damage whatever due to brown rotting in the fruit crop of Sib 3. The brown rot damage to the fruit of Elberta was less in the 1950–1951 and 1951–1952 crop but still very noticeable and high while the crop of Sib 3 was not damaged in the least except in a few cases during the very wet spell in the fall of 1951–1952 where a very few fruits showed a little breakdown caused by the stinging of wasps. These were so few that they could be considered very negligible. In all of these seasons and in all these numerous cases the fruits of Sib 3 showed a high degree of resistance to brown rot breakdown of the fruit. Elberta fruits proved highly susceptible.

Tests for keeping properties against brown rot fruit breakdown were made in all of the seasons listed above. In most cases fruits of Elberta lasted hardly more than twenty-four to forty-eight hours and only very few fruits kept for more than four days even under refrigeration. This prevailed mostly with the more mature and riper fruits but also to a significant degree with harder harvest ripe fruits. In contrast fruits of Sib 3 fully matured and dead ripe kept in average room temperatures to the middle of October until they dried up due to dehydration with no breakdown due to brown rotting. Most of the fruit of Sib 3 could be kept for an average of six weeks and then deterioration could be laid to dehydration but not to any rotting. These tests thus clearly established a significant difference in favor of Sib 3, over the Elberta in its high resistance to brown rot fruit breakdown.

It is of very much enhanced value to have the fruit of a nectarine that can be left on the tree to its maximum degree of ripening. This allows for the perfection of the fruit into a higher degree of delectability of quality, of larger size, of higher color, and for a longer unrushed picking season of the harvest, if so desired, and less need for the rush into refrigeration with its high costs. It has been repeatedly demonstrated that this new strain will hardly show any signs of brown rot or storage break down for a long period after fully tree ripened as compared to the behavior of the well known standard peach varieties. Fruit from this new strain ripened to a full rich sweet peachy maturity have been kept as much as three months in common refrigeration with the temperature around 35 to 40 degrees Fahrenheit. Such fruit held up for as much as twelve to fifteen days on display in a room temperature hovering above 75 degrees Fahrenheit. Most of the fruit in a temperature of 70 degrees Fahrenheit and over, commenced dehydrating without any break down and much of it finished up into an acceptable dehydrated product with no sign of brown rot or fermentatious break down. Fully tree ripened fruit of this new strain has been shipped via ordinary parcel post with no provision against heating in the warm spells of the earlier part of September to the middle of that month to distances of over 3,000 miles. Such fruit arrived with no brown rot or ferment breakdown after a period of three to five days en route and often as much as three days after arrival. Some of the fruit under such shipment with an occasional bruise in transit, did not break down in the area of the bruise, but tended to develop a non-objectional "jell" bruise with no sign of brown rot or ferment break down. It is imperative to pick the standard well known nectarine varieties that come under the usual nursery listings, in a "hard ripe" or slightly green pre-tree ripe state to insure some safety in keeping against brown rot break down. This is absolutely unnecessary for this new nectarine strain. This characteristic also, if it is found necessary to do so, stretches the whole harvesting, packing, storing and marketing season of the fruit, all of which is of increased economical value.

While the outstanding novel characteristics of this new variety of nectarine tree are of an intangible nature, the fruit color and other characteristics thereof are shown in the accompanying drawing and more particularly identified in the following detailed description in addition to that hereinabove set forth.

Tree. Large. Spreading. Vigorous. Very productive.

*Trunk.*—Stocky. Medium to shaggy, more shaggy with age.

*Height.*—Average for nectarine trees—fifteen to twenty feet.

*Leaves.*—Dark green. Slightly leathery. Length—6½ to 7 inches. Width—2 to 2½ inches. Large. Ovate. Lanceolate to spatulate.

*Buds.*—Obtuse. Plump. Pubescent Hardy. Large to medium.

*Flowers.*—Large pinkish light orchid. More showy than Elberta. Blooms about the same time as Elbertas, but are a shade or two deeper pink.

Fruit: As compared to the Elberta, is slightly smaller but heavier. Ripens at comparable times, but can be kept on the tree about two weeks later. Can be harvested, packed and shipped with relatively no later brown rot break down development. Its suture, stem, apex and base are substantially the same as the Elberta.

*Skin.*—Yellow. Highly red blushed. Similar to the skin of a plum. Absolutely devoid of any skin fuzz, down, or pubescence. Edible, very palatable and digestible.

*Flesh.*—Color—Golden Yellow. Smooth texture, rich agmigdalic fragrance and very firm. Richer flavor than Elberta.

*Cavity.*—Very small.

*Freestone qualities.*—Perfectly freestoned.

Stone: Free. Compared with the Elberta.

*Size.*—Considerably smaller.

*Length.*—Slightly shorter.

*Width.*—Slightly less.

*Thickness.*—About the same.

*Ventral edge.*—About the same. Compared with the nectarine tree in Plant Patent 479, the dorsal edge, base, tendency to split, color, and seeds are about the same.

*Shape.*—Oval to elliptical with very small ridges.

Resistance to:

*Arsenical sprays.*—Has an unusually high tolerance to the caustic effects of lead arsenical spray with tolerance allows for practically 100% control of curculio with relatively greater prospects for a better crop of well finished fruit.

*Insects.*—Same as the Elberta. However, its tolerance to lead arsenical sprays which kills insects makes this new nectarine tree less likely to sustain injury and damage from insects.

*Disease.*—Very high resistance to brown rot and storage break down. Very high resistance to any nectarine skin diseases.

*Cold.*—Hardier than Elberta to fruit bud winter kill, spring frost, and to any freeze injuries.

*Drought.*—Same as Elberta.

*Wind.*—Same as Elberta.

*Soil conditions.*—More vigorous grower than Elberta.

Storage qualities: Stores very well, even when picked fully tree ripened.

Ease of asexual reproduction: Can be budded as easily as other nectarines.

Canning qualities: Very good. Holds its shape well without breaking down. Not necessary to remove tender skin, but this can easily be done. The skin with its rich, peachy flavor and smooth character is edible and very palatable. This skin is highly edible in either the fresh or cooked state. Due to high flavor, it makes a very tasty canned item.

Use: Market, local, dessert, canning.

I claim:

A new and distinct variety of nectarine tree characterized as to novelty by its unusually high tolerance to the causticity of lead arsenical spray and thereby allowing for relatively higher curculio worm control than other nectarine or peach tree varieties and strains, by the non-fuzz, plum-like waxy and smoother skin of its fruit, a highly flavored edible, digestable, palatable skin, the winter hardiness of the tree, the greater resistance of the fruit bud to winter kill, spring frosts and to any freeze injuries, the resistance to brown rot and storage break down, the high resistance to any nectarine or peach skin diseases, the high holding up properties of the fruit in all harvest to market operations, and the firmness, and flavor of the flesh of the fruit, substantially as described.

FREDERICK WENZL HOF MANN.

References Cited in the file of this patent

UNITED STATES PATENTS

| Number | Name | Date |
|---|---|---|
| Pl. Pt. 479 | Hof Mann | July 22, 1941 |